US009121789B2

(12) United States Patent
Stanley et al.

(10) Patent No.: US 9,121,789 B2
(45) Date of Patent: Sep. 1, 2015

(54) LASER BASED LENS ANALYSIS DEVICE AND METHOD

(71) Applicants: Christine Stanley, Lexington Park, MD (US); Adam Carlisle, Lexington Park, MD (US)

(72) Inventors: Christine Stanley, Lexington Park, MD (US); Adam Carlisle, Lexington Park, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 14/048,488

(22) Filed: Oct. 8, 2013

(65) Prior Publication Data

US 2015/0098078 A1 Apr. 9, 2015

(51) Int. Cl.
*G01B 9/00* (2006.01)
*G01M 11/02* (2006.01)
*G01N 9/00* (2006.01)

(52) U.S. Cl.
CPC .............. *G01M 11/0228* (2013.01); *G01N 9/00* (2013.01)

(58) Field of Classification Search
CPC .................... F16F 9/0418; G01R 33/34046
USPC ................. 356/237.1–237.5, 239.1, 124; 382/100–104, 115–118, 154
See application file for complete search history.

(56) References Cited

U.S. PATENT DOCUMENTS

2014/0152792 A1* 6/2014 Krueger ...................... 348/78
2014/0233024 A1* 8/2014 Taniguchi et al. ......... 356/237.5

* cited by examiner

*Primary Examiner* — Gregory J Toatley
*Assistant Examiner* — Iyabo S Alli
(74) *Attorney, Agent, or Firm* — Mark O. Glut; NAWCAD

(57) ABSTRACT

A laser based lens analysis device comprising of a laser for emitting a laser beam, a beam expander for increasing the diameter of the laser beam, a beam collimator for collimating the increased diameter laser beam, an aperture for controlling the collimated laser beam and rendering the collimated laser beam to be substantially symmetrical, and a beam profiler for analyzing the laser beam characteristics after the controlled-symmetrical laser beam passes through the lens being tested. A method for lens analysis comprising the steps of emitting a laser beam, increasing the diameter of the laser beam, collimating the increased diameter laser beam, rendering the collimated laser beam substantially symmetrical, directing the symmetrical laser beam towards the lens being tested, and analyzing characteristics of the directed laser beam after the directed laser beam passes through the lens being tested.

8 Claims, 2 Drawing Sheets

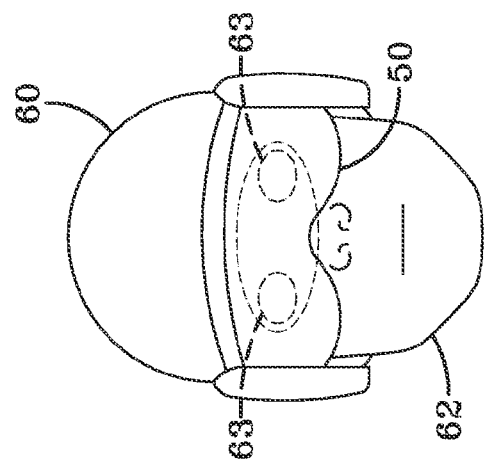
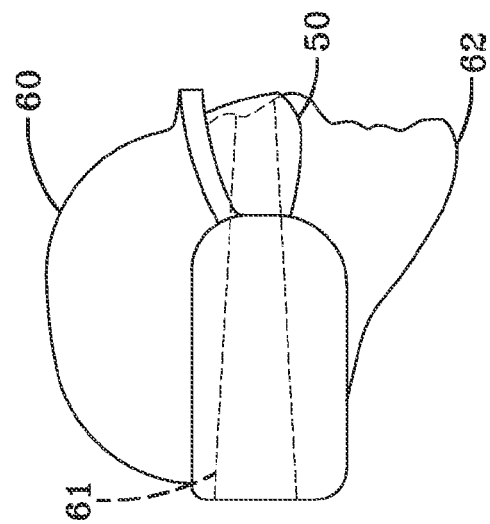
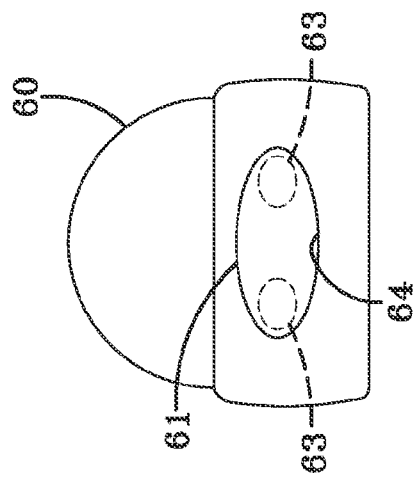

LASER BASED LENS ANALYSIS DEVICE AND METHOD

STATEMENT OF GOVERNMENT INTEREST

The invention described herein may be manufactured and used by or for the Government of the United States of America for governmental purposes without payment of any royalties thereon or therefor.

BACKGROUND

A lens is, but without limitation, a piece of glass or other transparent substance with curved or flat surfaces for concentrating and/or dispersing light rays. A lens may be convex or concave. Lenses are typically used in eyeglasses, visors, cameras, microscopes, and telescopes, etc. Lenses and devices utilizing a lens or lenses are tested for optical quality to ensure they are within required specifications. Optical quality includes prism, spherical, and cylindrical power. Prism describes the phenomena that moves an object in any direction other than where it should appear in real space. Refractive powers are spherical and cylindrical. Spherical power makes an object appear larger or smaller than what it should appear in real space i.e., reading glasses are positive spherical powered lenses. Cylindrical power makes an object elongated into a cylinder shape.

Currently a lensometer is used to analyze and test lenses and devices utilizing a lens. Many devices under test by the Department of Navy are physically too large or oddly shaped to properly fit in a lensometer. Additionally, lensometers cannot adequately test the combined optical power of stacked lenses or multiple substrates of lenses, like a pair of spectacles placed behind a visor. Lensometers cannot physically or optically accommodate testing through multiple substrates or differentiate the power attributed to each substrate. Lensometers cannot analyze a series of lenses.

SUMMARY

The present invention is directed to a laser based lens analysis device and method that meets the needs enumerated above and below.

The present invention is directed to a laser based lens analysis device comprising of a laser for emitting a laser beam, a beam expander for increasing the diameter of the laser beam, a beam collimator for collimating the increased diameter laser beam, an aperture for controlling the diameter of the collimated laser beam and rendering the collimated laser beam to be substantially symmetrical prior to passing through the lens being tested, and a beam profiler for analyzing the laser beam characteristics after the controlled-symmetrical laser beam passes through the lens being tested.

It is a feature of the present invention to provide a laser based lens analysis device and method that can effectively test stacked lenses or devices that utilize a lens or lenses.

It is a feature of the present invention to provide a laser based lens analysis device and method that can test prism, cylindrical, and spherical power of a lens, stacked lenses, or devices that utilize a lens or a series of lenses.

It is a feature of the present invention to provide a laser based lens analysis device and method that can test and analyze optically stacked items in the as worn position, especially in head mounted configurations.

DRAWINGS

These and other features, aspects and advantages of the present invention will become better understood with reference to the following description and appended claims, and accompanying drawings wherein:

FIG. 2a is a rear view of an embodiment of the helmet, head form, and visor configuration;

FIG. 2b is a side view of an embodiment of the helmet, head form, and visor configuration; and, FIG. 2c is a front view of an embodiment of the helmet, head form, and visor configuration.

DESCRIPTION

Figure 1:
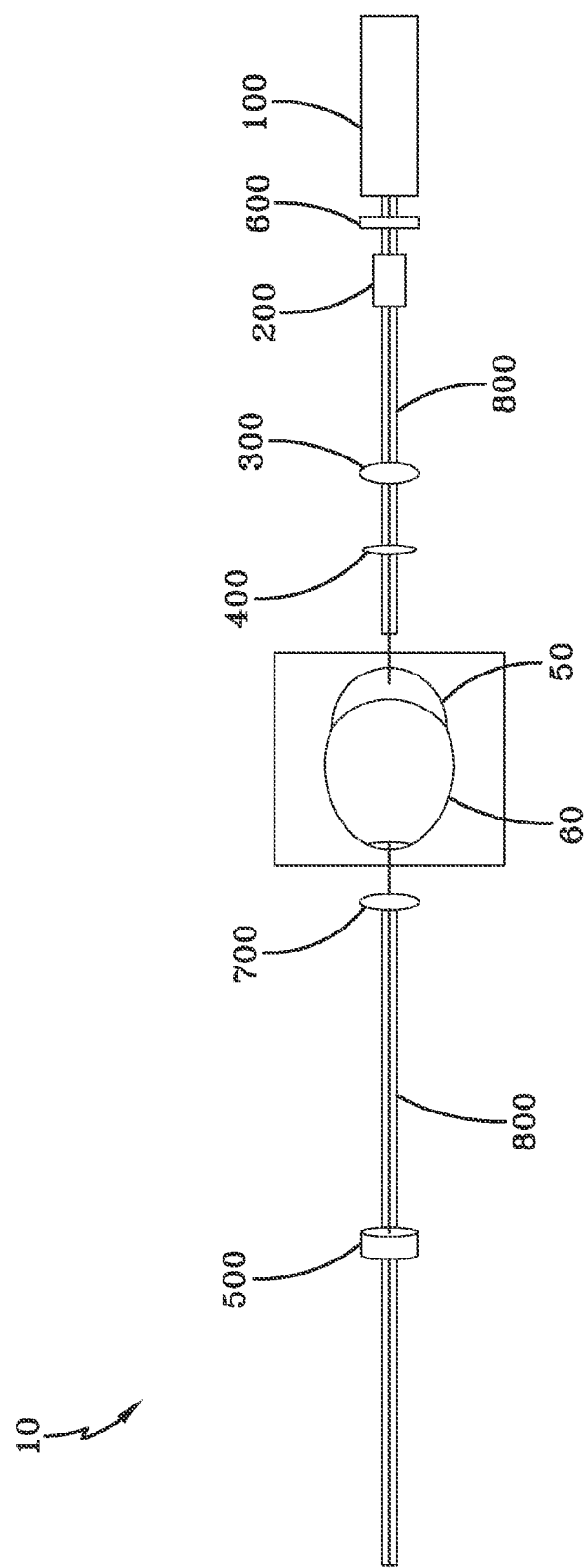
FIG. 1 is a top view of an embodiment of the laser based lens analysis device.

The preferred embodiments of the present invention are illustrated by way of example below and in FIGS. 1-2. As shown in FIG. 1, the laser based lens analysis device 10 comprises of a laser 100 for emitting a laser beam, a beam expander 200 for increasing the diameter of the laser beam, a beam collimator 300 for collimating the increased diameter laser beam, an aperture 400 for controlling the diameter of the collimated laser beam and rendering the collimated laser beam to be substantially symmetrical prior to passing through the lens 50 being tested, and a beam profiler 500 for analyzing the laser beam characteristics after the controlled-symmetrical laser beam passes through the lens 50 being tested.

In the description of the present invention, the invention will be discussed in an aircraft environment, specifically for a helmet 60 donned with a visor 50 as shown in FIG. 1; however, this invention can be utilized for any type of application that requires use of a lens analysis device.

In one of the preferred embodiments of the invention, the preferred laser 100 is a 5 mW tunable helium neon laser or any other type of continuous wave laser. The beam expander 200 may be a 10× microscope objective expander. The beam collimator 300 may be a 16 cm focal length converging lens placed 16 cm in from of the beam expander 200. However, any type of laser 100, beam expander 200, or beam collimator 300 that is practicable may be utilized.

A beam collimator 300 may be defined, but without limitations, as a device that prevents divergence of a laser beam. The aperture 400 is for controlling the diameter of the laser beam and rendering the laser beam to be substantially symmetrical. An aperture 400 may be defined, but without limitation, as an opening, a hole, a gap, or a space through which light passes in an optical or photographic instrument. A symmetrical beam may be defined, but without limitation, as a laser beam where the energy is distributed substantially evenly throughout the diameter of the laser beam.

The laser based lens analysis device 10 may also include a filter 600 for decreasing power of the laser beam prior to entering the beam expander 200. The preferred filter 600 is a neutral density filter. A neutral density filter 600 may be defined, but without limitation, as a filter that uniformly reduces or modifies the intensity of all wavelengths or colors of light equally, giving no changes in hue differences of color rendition in lens being tested. The neutral density filter 600 can be a colorless (clear) neutral density or grey filter. The preferred neutral density filter 600 is a 1 OD neutral density filter.

The laser based lens analysis device 10 can also include a focusing lens 700 for focusing the laser beam toward the beam profiler 500 after the laser beam passes through the lens 50 being tested. The laser based lens analysis device 10 may also include a track 800 for holding the laser 100, the neutral density filter 600, the beam expander 200, the beam collimator 300, the aperture 400, the lens 50 being tested, the focusing lens 700, and the beam profiler 500, such that the laser 100, the neutral density filter 600, the beam expander 200, the beam collimator 300, the aperture 400, the lens 50 being tested, the focusing lens 700, and the beam profiler 500 can be moved on different locations along the track 800. However, the laser 100, lens 50, and helmet 60 may be positioned in an area not on the track 800 or in a break in the track 800. In one of the preferred embodiments, the laser 100 is bolted to an optical table for stability. The lens 50 being tested may be optionally either secured to the helmet 60 or in a holder that is secured on a motorized stage configuration with X, Y and rotation axis secured (not moveable) to the optical table for stability.

As shown in FIGS. 1, 2a, 2b, and 2c, the laser based lens analysis device 10 can also include a head form 62 donned with a helmet 60, the lens 50 being tested positioned on the helmet like a visor, the head form 62 and the helmet 60 having at least one passage 61 such that the laser beam can pass through both the head form 62 and helmet 60 and be directed toward the beam profiler 500. The passage 61 is typically unobstructed such that laser beam may pass the head form 62 without any interference to the laser beam after it passes through the lens 50 being tested. In the preferred embodiment, the head form 62 is an anthropometric head form, typically in the 50% adult range. In one of the preferred embodiments, two passageways 63 or holes are drilled where eyes are supposed to be, connecting to a single larger passage 64 or hole exiting the back of the head form 62. Spectacles may be placed on head form 62 to simulate a person wearing glasses. The lens 50 being tested may be different types of pilot visors, a visor fitted with night vision filter(s), or any type of lens alone or in combination with another lens.

The beam profiler 500 may be a card with a calibrated grid that shows or describes changes in laser beam characteristics such as, but without limitation, the size, shape and structure of the laser beam. The beam profiler 500 may also be computer controlled or a charge couple device camera.

The laser based lens analysis device 10 may also be attached to a computer that includes a software beam profiler program. The computer can include a program that analyzes the laser beam's shape, size, and location. In the preferred embodiment, the laser 100 is stand alone with a beam profiler 500; however, a single computer can control the laser beam and beam profiler 500.

In operation, the method for lens analysis, particularly for measuring prism power comprises of the steps of emitting a laser beam, increasing the diameter of the laser beam, collimating the increased diameter laser beam, rendering the collimated laser beam to be substantially symmetrical, directing the symmetrical beam towards the lens being tested, and analyzing the laser beam characteristics after the directed laser beam passes through the lens being tested. Another embodiment of the method, particularly for measuring spherical and cylindrical power, includes emitting a laser beam, decreasing power of the laser beam, increasing the diameter of the decreased power laser beam, collimating the increased diameter laser beam, rendering the collimated beam symmetrical, directing the symmetrical beam towards the lens being tested, focusing the laser beams, and analyzing the laser beam characteristics after the controlled laser beam passes through the lens being tested.

When introducing elements of the present invention or the preferred embodiment(s) thereof, the articles "a," "an," "the," and "said" are intended to mean there are one or more of the elements. The terms "comprising," "including," and "having" are intended to be inclusive and mean that there may be additional elements other than the listed elements.

Although the present invention has been described in considerable detail with reference to certain preferred embodiments thereof, other embodiments are possible. Therefore, the spirit and scope of the appended claims should not be limited to the description of the preferred embodiment(s) contained herein.

What is claimed is:

1. A laser based lens analysis device comprising:
   a continuous wave laser for emitting a laser beam, the laser beam having a diameter;
   a beam expander for increasing the diameter of the laser beam;
   a beam collimator for collimating the increased diameter laser beam;
   an aperture for controlling the collimated laser beam and rendering the collimated laser beam substantially symmetrical; and,
   a beam profiler for analyzing laser beam characteristics of the controlled-symmetrical laser beam after the controlled-symmetrical laser beam passes through the lens being tested.

2. The laser based lens analysis device of claim 1, wherein the device further comprises a neutral density filter for decreasing power of the laser beam prior to entering the beam expander.

3. The laser based lens analysis device of claim 2, wherein the device further comprises a focusing lens for focusing the controlled-symmetrical laser beam toward the beam profiler after the controlled-symmetrical laser beam passed through the lens being tested.

4. The laser based lens analysis device of claim 3, wherein the device further comprises a track for holding the neutral density filter, the beam expander, the beam collimator, the aperture, the focusing lens, and the beam profiler, such that the neutral density filter, the beam expander, the beam collimator, the aperture, the focusing lens, and the beam profiler are moveable on different locations along the track.

5. The laser based lens analysis device of claim 1, wherein the device further comprises a head form donned with a helmet, the lens being tested positioned on the helmet like a visor, the head form and the helmet having at least one passage such that the laser beam can pass through both the head form and helmet and be directed toward the beam profiler.

6. A method for lens analysis comprising the steps of:
   emitting a laser beam with a continuous wave laser, the laser beam having a diameter;
   increasing the diameter of the laser beam;
   collimating the increased diameter laser beam;
   rendering the collimated laser beam substantially symmetrical;
   directing the symmetrical laser beam towards the lens being tested; and,
   analyzing characteristics of the directed laser beam after the directed laser beam passes through the lens being tested.

7. A method for lens analysis comprising the steps of:
   emitting a laser beam with a continuous wave laser, the laser beam having a diameter;
   limiting power of the laser beam;
   increasing the diameter of the limited power laser beam;
   collimating the increased diameter laser beam;
   rendering the collimated laser beam symmetrical;
   limiting the diameter of the symmetrical laser beam;
   focusing the laser beam; and,
   analyzing characteristics of the laser beam after the focused laser beam passes through the lens-being tested.

8. The method of claim 7, wherein the lens being tested is donned on an anthropometric head form, the head form includes a passageway such that the laser beam can pass through the head form in order to for the laser beam to be analyzed.

* * * * *